United States Patent
Chuter et al.

(10) Patent No.: US 6,652,580 B1
(45) Date of Patent: Nov. 25, 2003

(54) MODULAR, STAGED GRAFT AND ATTACHMENT SYSTEM FOR ENDOVASCULAR REPAIR

(75) Inventors: Timothy A. M. Chuter, Burlingame, CA (US); David T. Pollock, Redwood City, CA (US); Tamara L. Trayer, Belmont, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/565,359

(22) Filed: May 5, 2000

Related U.S. Application Data

(62) Division of application No. 09/469,341, filed on Dec. 20, 1999, now Pat. No. 6,293,969, which is a continuation of application No. 09/014,945, filed on Jan. 28, 1998, now Pat. No. 6,030,415.
(60) Provisional application No. 60/036,518, filed on Jan. 29, 1997.

(51) Int. Cl.⁷ .................................................. A61F 2/06
(52) U.S. Cl. ....................... 623/1.36; 623/1.13; 606/194
(58) Field of Search ................................ 623/1.1, 1.14, 623/1.35, 1.36, 1.11, 1.13, 1.23, 1.25; 606/153, 191, 194, 195, 198; 600/36

(56) References Cited

U.S. PATENT DOCUMENTS

| | | | |
|---|---|---|---|
| 5,035,706 A | | 7/1991 | Gianturco |
| 5,064,435 A | | 11/1991 | Porter |
| 5,354,309 A | * | 10/1994 | Schnepp-Pesch et al. ... 606/198 |
| 5,387,235 A | | 2/1995 | Chuter |
| 5,507,771 A | | 4/1996 | Gianturco |
| 5,562,724 A | | 10/1996 | Vorwerk et al. |
| 5,575,817 A | | 11/1996 | Martin |
| 5,632,772 A | | 5/1997 | Alcime et al. |
| 5,639,278 A | | 6/1997 | Dereume et al. |
| 5,643,312 A | * | 7/1997 | Fischell et al. ............. 606/198 |
| 5,653,743 A | | 8/1997 | Martin |
| 5,676,696 A | | 10/1997 | Marcade |
| 5,683,449 A | | 11/1997 | Marcade |
| 5,683,450 A | | 11/1997 | Goicoechea et al. |
| 5,713,917 A | | 2/1998 | Leonhardt et al. |
| 5,716,365 A | | 2/1998 | Goicoechea et al. |
| 5,718,724 A | | 2/1998 | Goicoechea et al. |
| 5,728,131 A | | 3/1998 | Frantzen et al. |
| 5,769,887 A | | 6/1998 | Brown et al. |
| 5,776,180 A | | 7/1998 | Goicoechea et al. |
| 5,782,904 A | * | 7/1998 | White et al. ............... 623/1.13 |
| 5,800,508 A | | 9/1998 | Goicoechea et al. |
| 5,824,034 A | | 10/1998 | Schmitt et al. |
| 5,824,037 A | | 10/1998 | Fogarty et al. |

(List continued on next page.)

FOREIGN PATENT DOCUMENTS

FR        2 748 197 A1    11/1997

*Primary Examiner*—David J. Isabella
*Assistant Examiner*—Urmi Chattopadhyay
(74) *Attorney, Agent, or Firm*—Fulwider Patton Lee & Utecht, LLP

(57) ABSTRACT

A system for repairing body lumens including a modular graft and a method for deploying the graft within the body lumen. The modular graft includes a first component having first and second legs portions which mate with second and third graft components, respectively. The second leg portion has a bell bottom shape. The modular graft further includes expandable members which aid in implanting the modular graft as well as facilitates the mating of its components. In order to repair the body lumen, the first component is placed at the repair site and thereafter the first and second legs are advanced to the repair site and attached to the first component. A further aspect of the invention is a fixation device which is adapted to perform an attachment function. The graft and the fixation device are configured to be axially separated from one another so as to allow the graft to attach to the vascular wall proximal of the graft.

24 Claims, 12 Drawing Sheets

U.S. PATENT DOCUMENTS

| | | |
|---|---|---|
| 5,824,042 A | 10/1998 | Lombardi et al. |
| 5,851,228 A * | 12/1998 | Pinheiro .................. 623/1 |
| 5,855,598 A | 1/1999 | Pinchuk |
| 5,916,263 A | 6/1999 | Goicoechea et al. |
| 5,938,696 A | 8/1999 | Goicoechea et al. |
| 5,948,017 A * | 9/1999 | Taheri .................. 623/1.14 |
| 5,993,481 A | 11/1999 | Marcade et al. |
| 6,015,431 A | 1/2000 | Thornton et al. |
| 6,051,020 A | 4/2000 | Goicoechea et al. |
| 6,099,558 A | 8/2000 | White et al. |
| 6,102,938 A | 8/2000 | Evans et al. |
| 6,102,940 A | 8/2000 | Robichon et al. |
| 6,117,167 A | 9/2000 | Goicoechea et al. |
| 6,123,722 A | 9/2000 | Fogarty et al. |
| 6,149,682 A | 11/2000 | Frid |
| 6,152,956 A | 11/2000 | Pierce |
| 6,221,102 B1 * | 4/2001 | Baker et al. .................. 623/1.36 |
| 6,241,759 B1 * | 6/2001 | Piplani et al. .................. 623/1.11 |
| 6,361,556 B1 * | 3/2002 | Chuter .................. 623/1.11 |

\* cited by examiner

IPSILATERAL FEMORAL ARTERY

CONTRALATERAL FEMORAL ARTERY

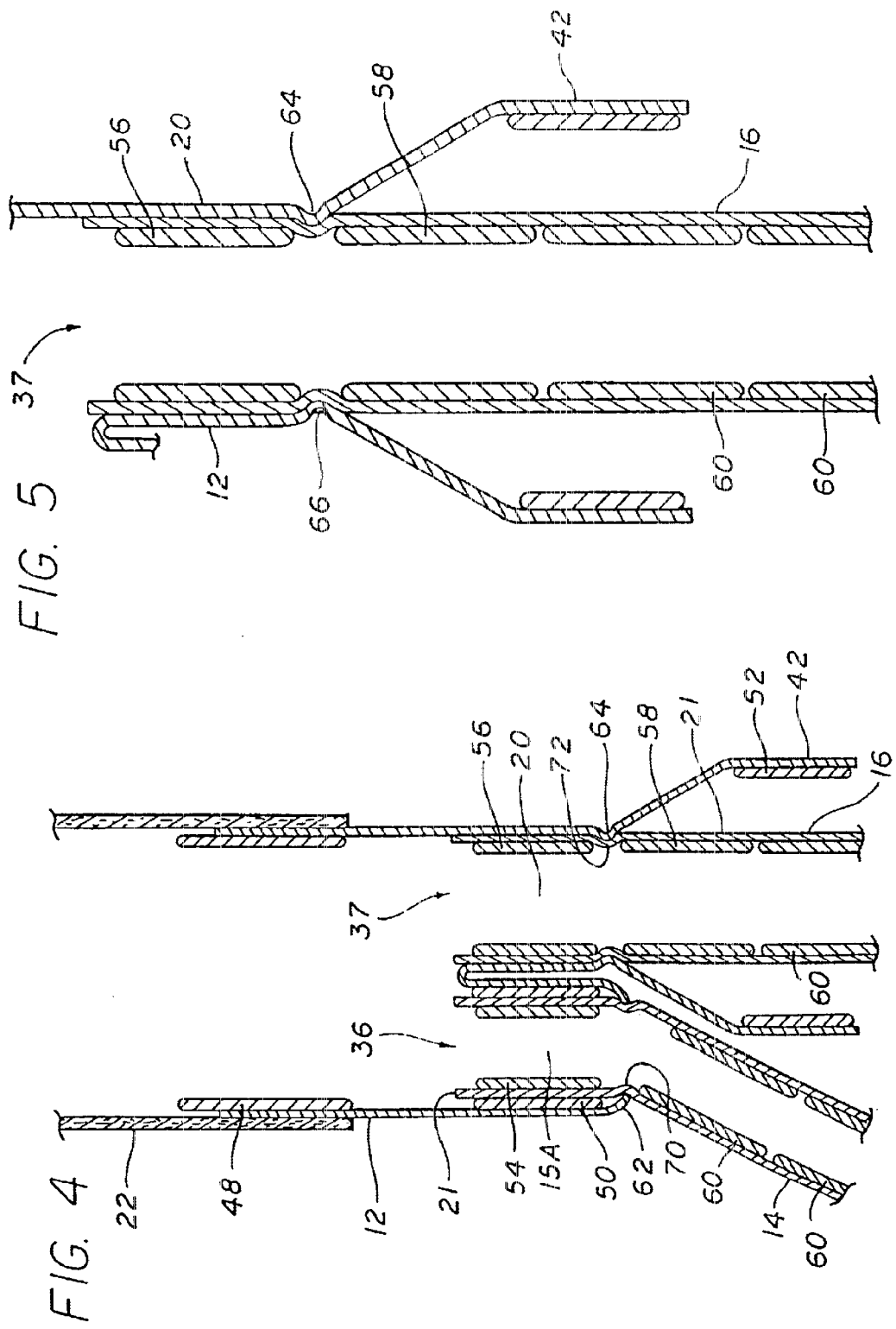

MODULAR, STAGED GRAFT AND ATTACHMENT SYSTEM FOR ENDOVASCULAR REPAIR

This application is a continuation-in-part of application Ser. No. 09/469,341, filed Dec. 20, 1999, now U.S. Pat. No. 6,293,969, which is a continuation of application Ser. No. 09/014,945 filed Jan. 28, 1998, now U.S. Pat. No. 6,030,415, which is based on Provisional Application No. 60/036,518 filed Jan. 29, 1997.

FIELD OF THE INVENTION

The present invention is directed to an intraarterial prosthesis, a modular stent-graft, for repair of abdominal aortic aneurysm ("AAA" herein). Moreover, the present invention relates to a graft which embodies a reduced profile in its compressed condition as well as to facilitating the insertion, in vivo, of one element of a modular graft into another.

BACKGROUND OF THE INVENTION

An intraarterial prosthesis for the repair of AAAs (grafts) is introduced into the AAA through the distal arterial tree in catheter-based delivery systems, and is attached to the non-dilated arteries proximal and distal to the AAA by an expandable framework (stents). An intraarterial prosthesis of this type has two components: a flexible conduit, the graft, and the expandable framework, the stent (or stents). Such intraarterial prosthesis used to repair AAAs is named stent-graft. AAAs typically extend to the aortic bifurcation of the common iliac arteries. There is rarely any non-dilated aorta below the aneurysm. If there is not then the distal end of the graft must be implanted in the lilac arteries, and for the graft to maintain prograde in-line flow to the legs and arteries of the pelvis, it must also bifurcate. Currently available stent-grafts fall into several categories. One category of grafts are those in which a preformed graft (either tube, aorto-mono-iliac or bifurcated) is inserted whole into the arterial system and manipulated into position about the AAA. This is a unibody graft. Another category of stent-grafts are those in which a graft is assembled in situ from two or more stent-graft components. This latter stent-graft is referred to as a modular stent-graft.

The use of modular stent-grafts may be attended by a number of problems. Generally, modular stent-grafts must be compressed for insertion and delivery into the vascular system in a delivery capsule. It will be appreciated that the larger the outer profile of the graft in its compressed condition, the more difficult it will be to insert the device into vasculature and to negotiate the twists and turns of the vasculature. Another significant problem is that, because of the restricted geometry of the vasculature, it can be difficult to insert one element of a modular stent-graft into another. Yet a further problem is that the aorta proximate the renal arteries can lack adequate healthy tissue for forming an attachment of the graft to the aortic wall.

Accordingly, there exists a need to provide a modular graft that can assume a profile better suited for navigating tortuous vasculature, and that is configured to facilitate assembly of its subcomponents. There is a further need to provide an apparatus which can be used where there is insufficient healthy aortic tissue near the renal arteries and which permits a fixation device thereof to be axially rotated with respect to the graft. The device of the present invention addresses these and other needs.

SUMMARY OF THE INVENTION

Briefly, and in general terms, the present invention is directed to a modular stent-graft comprising multi-components. The modular stent-graft of the present invention eliminates or avoids the main drawbacks common to the currently available modular stent-grafts for repair of AAAs. Stent-grafts are inserted into the AAA through the femoral arterial system. The graft must bridge the AAA and form a leak-proof conduit between the aorta and the iliac arteries. The surgeon can only view the operation by X-ray techniques and yet the surgery is performed in a three-dimensional environment. This is a demanding regime and requires a trained and skilled surgeon.

The main drawbacks common to the current modular stent-grafts are:

1. The connection site between the stent-graft components is prone to leakage and a separation of the components which allows blood to leak directly into the AAA restoring the potential for rupture. If the AAA ruptures, the result is frequently the death of the patient.
2. The connection site on the first stent-graft component is often difficult to catheterize prior to introduction of the second stent-graft component. The necessary instrumentation required to insert catheters and carry out the repair of the abdominal aneurysm can dislodge mural thrombus in the AAA. The dislodged mural thrombus is carried in the blood flow through the femoral arteries to small distal arteries causing blockage and tissue necrosis.
3. Modular stent-grafts are conventionally prepared for delivery with one or more stents positioned within a lumen of the graft, thus substantially adding to the profile of the stent-graft assembly. Moreover, additional stents positioned in separate branches of a bifurcated graft are conventionally located at the same axial level, thus adding to the profile of the graft. Further, due to the nature of modular stent-grafts, it is sometimes difficult to assemble, in vivo, the various components of conventional stent-grafts. These factors add to the difficulty of inserting and delivering a graft within the vasculature of a patient.

The modular stent-graft of the present invention consists of at least three stent-graft components. The first stent-graft component resembles a pair of shorts with the trunk proximal and the two legs or docking sites distal. The second and third stent-graft components are tubes of almost uniform diameter that extend from the primary stent-graft component docking sites, through the AAA, to the iliac arteries. The completed modular stent graft bridges the AAA from the abdominal aorta to the iliac arteries. The proximal ends of the second and third stent-graft components, i.e., ends nearest the aorta, are inserted into the docking sites of the primary stent-graft. The second stent-graft component is inserted through the ipsilateral arteries to the ipsilateral docking site of the primary stent-graft component. The second stent-graft is also referred to as the ipsilateral extension. The third stent-graft component is inserted through the contralateral arteries to the contralateral docking site through the bell-bottom portion of the primary stent-graft component. The third stent-graft is also referred to as the contralateral extension. Further extensions can be added to any of the stent-graft components to lengthen the overall system.

The modular stent-graft of the present invention has a number of distinguishing elements. The stents that hold the two docking sites open are at different levels and are of different sizes. On the ipsilateral docking site, the stent is within the docking site. With regard to the contralateral docking site, the stent is within a wider distal segment, the bell-bottom segment below the contralateral docking site.

Because the distal stents of the primary stent-graft component are at different levels, one below the other, they occupy different segments of the delivery system. Since the stent-graft components are delivered to the AAA through a narrow catheter, they must be reduced to the smallest possible diameter to effect and ease delivery. By separating the stent-graft into three components, the necessary stents can be arranged at different levels permitting them to be as large as possible. Since the distal stents can be larger in a modular system than in a unitary system, the distal orifice of the ipsilateral and contralateral docking site can be large and thus easier to catheterize for the delivery. This is only important on the contralateral side, that is, the side with the contralateral docking site. On the ipsilateral side, that is, the side with the ipsilateral docking site, catheters can be introduced over the same guide wire that was used to introduce the first stent-graft component through the arterial system to the AAA. In practice, the distal orifice of the contralateral docking site can be at least as large as the trunk of the primary stent-graft component. The first stent-graft component and the second and third stent-graft components and can be made of the same different biologically inert graft and stent material, such as biologically inert knit or woven fabric, or membrane material, such as PTFE membrane material, and springy material, such as stainless steel or titanium.

In a further aspect of the present invention, an expandable framework configured to attach a primary stent-graft component to vasculature is axially separated from the graft, the same being connected to the graft by flexible longitudinally extending members, or ties. Where the graft and expandable framework are thus separated, additional expandable frameworks may be added to the graft after deployment of the graft to perform the function of sealing the graft to vascular wall and/or to maintain the patency of the graft.

An advantage of providing a fixation device axially separated from the graft, and providing support structures after deployment of the graft within vasculature, is that the unassembled components of the graft assembly can assume a smaller profile for insertion into vasculature than would a fully assembled stent-graft. This improvement is further enhanced by placing at different levels, stents adapted to maintain the patency of the graft.

In one aspect of the invention, the flexible longitudinally extending members may be of such a length that an end of the graft abuts the fixation device. Alternatively, the flexible longitudinally extending members may be of sufficient length to provide a gap between the fixation device and the graft. In both embodiments, the fixation device can assume a different diameter than the graft and an axis of the graft can be at an angle with respect to an axis of the fixation device. By permitting this axial angulation, the graft device can be placed in angulated necks and an effective seal with the vascular wall can be better achieved.

These and other advantages of the invention will become more apparent from the following detailed description of the preferred embodiments. When taken in conjunction with the accompanying exemplary drawings the person of skill in the art will appreciate that various embodiments incorporate the present invention.

BRIEF DESCRIPTION OF THE DRAWINGS

FIG. 4 is a top fragmentary cross-sectional view of the stent-graft of FIG. 1;

FIG. 5 is an enlarged fragmentary cross-sectional view of the connection between the first stent-graft component and the third stent-graft component of the stent-graft of FIG. 1;

DETAILED DESCRIPTION OF THE PREFERRED EMBODIMENTS

Figure 1:
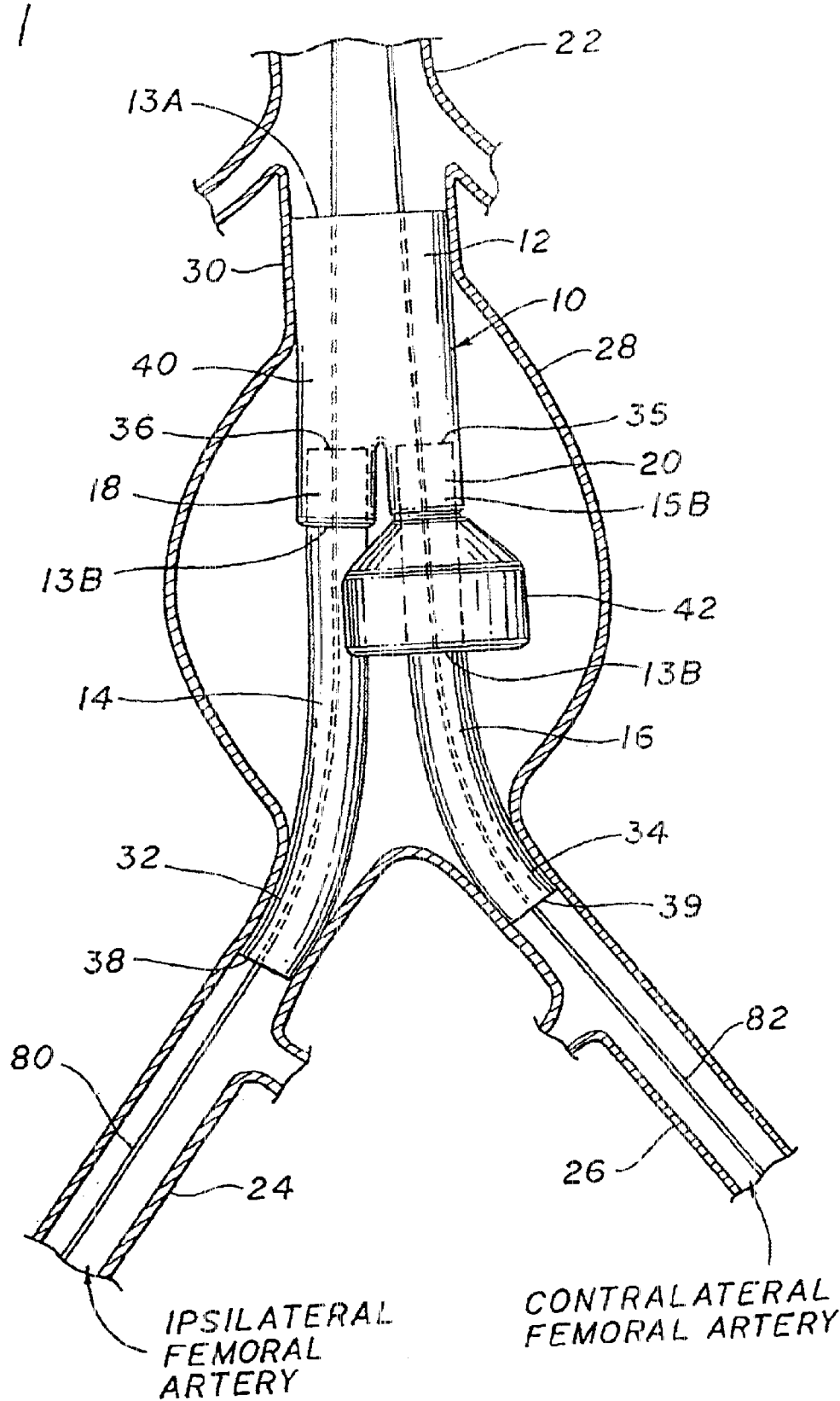
FIG. 1 is a cross-sectional view of the modular stent-graft of the present invention implanted to repair an abdominal aortic aneurysm.

Referring to FIG. 1, the modular stent-graft 10 of the present invention is illustrated implanted to repair an abdominal aorta aneurysm 28. The modular stent-graft 10 comprises a first stent-graft component 12 having a proximal end 13A and a distal end 13B, second stent-graft component 14, often referred to as the ipsilateral extension, and a third stet-graft component 16, often referred to as the contralateral extension. The three components comprise sheaths or grafts 41, 21 and 23 containing self-expanding stents (not shown in FIG. 1). The proximal end 13A of the trunk 40 of the first stent-graft component 12 is implanted in the proximal implantation site 30 in a non-dilated portion of the abdominal aorta 22. To aid in affixing the proximal end 13A to the abdominal aorta 12, a fixation device may be employed. In one aspect of the invention, the fixation device 100 is attached to the first stent-graft component 14 so that it is positioned superior to the proximal end 13A and as shown in FIG. 1, the fixation device 100 may be configured suprarenally. The proximal end 36 of the second stent-graft component, or ipsilateral extension, is connected to the first stent-graft component at the ipsilateral docking site 18. The proximal end 35 of the third stent-graft component 16, or contralateral extension, is connected to the contralateral docking site 20. The distal end 38 of the second stent-graft component is implanted in the undilated portion of the ipsilateral iliac artery 24 at the ipsilateral distal implantation site 32. The distal end 39 of the third stent-graft component, or contralateral extension, is implanted in a non-dilated portion of the contralateral iliac artery 26 at contralateral distal implantation site 34, as will be described herein. The contralateral leg 15B of the first stent-graft component terminates in a bell-bottom 42. Bell-bottom aids in the surgical implantation and manipulation of the modular stent-graft in the aorta and the aneurysm 28 as will be described below.

The ipsilateral catheter guide wire 80 is shown coming up from the ipsilateral arteries (the ipsilateral femoral artery and ipsilateral iliac artery) into the ipsilateral extension through the ipsilateral docking site and out through the proximal end 13A of the trunk 40. The contralateral catheter guide wire 82 is shown extending up from the contralateral femoral artery through the contralateral iliac artery and through the contralateral extension 16 through the contralateral docking site 20 and out through the proximal end 13A of the trunk 40. Normally, both guide wires are left in until the completion of the operation. After the modular stent-graft has been successfully implanted to repair the abdominal aortic aneurysm, the guide wires are removed. In the preferred embodiment, the ipsilateral catheter guide wire 80 is first inserted to permit the delivery of the first stent-graft component and the ipsilateral extension into the AAA. The contralateral catheter guide wire 82 is inserted from the contralateral iliac artery 26 into the contralateral docking site 20 of the first stent-graft component. As mentioned above, the surgeon is viewing the three-dimensional environment of the AAA with a two-dimensional x-ray screen. The large bell-bottom 42 of the first stent-graft component eases the surgeon's task in successfully snaking the guide wire 82 up into the bell-bottom 42 and into the contralateral docking site 20. Obviously when the first guide wire 80 is inserted, the surgeon is concerned with having the guide wire come out of the ipsilateral iliac artery 24 through the AAA into the abdominal aorta 22. Without the bell-bottom 42 below the contralateral docking site 20, it would be very difficult, and in many instances impossible, to successfully snake the contralateral catheter guide wire 82 into the contralateral docking site 20 of the first stent-graft component.

Figure 2:
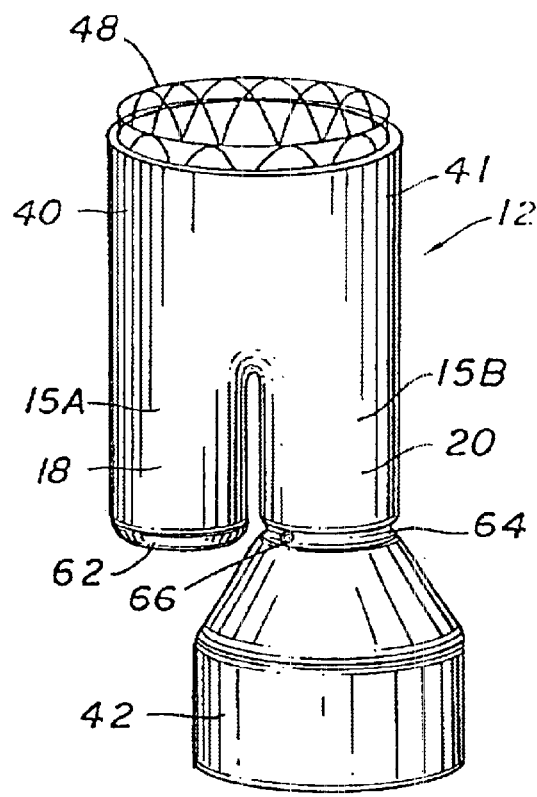
FIG. 2 is a front perspective view of the first stent-graft component of the modular stent-graft of FIG. 1.
Figure 3:
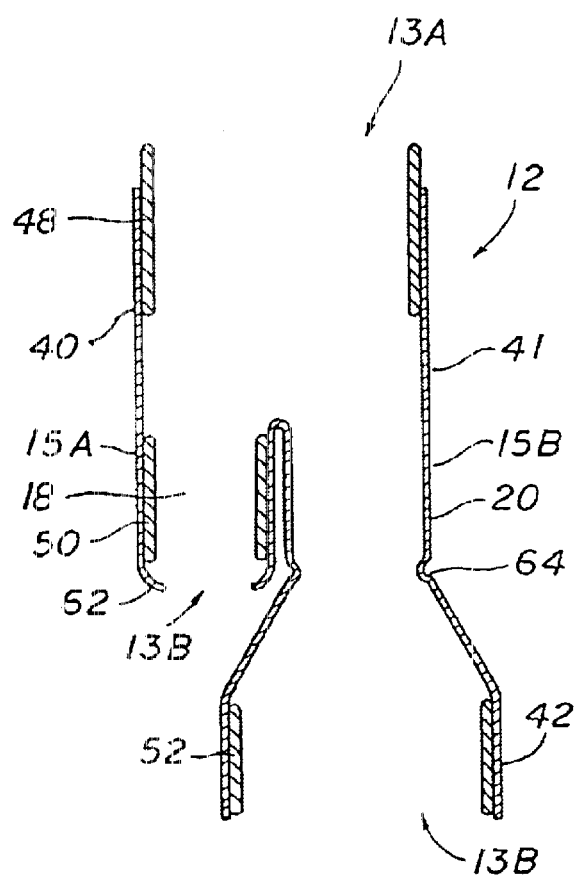
FIG. 3 is a cross-sectional view of the first stent-graft component of FIG. 2.

Referring to FIGS. 2 and 3, the first stent-graft component 12 of the modular stent-graft 10 comprises a trunk 40 at the proximal end 13A of the first stent-graft component and ipsilateral leg 15A and contralateral leg 15B at the distal end 13B of the first stent-graft component. Optionally, the distal end of the ipsilateral leg 15A has a constricted portion 62. Optionally, the contralateral leg 15B has a constricted portion 64 at approximately the same level as constricted portion 62. A radioopaque marker 66 is placed on the first stent-graft component in the constricted portion 64, if present, adjacent the constricted portion 62, as shown in FIG. 2. This marker aids the surgeon in positioning the proximal stents of the ipsilateral and contralateral extensions. The first stent-graft component is delivered into the aorta aneurysm 28 via a conventional stent-graft catheter delivery system, such as disclosed in U.S. Pat. Nos. 4,580, 568; 4,655,771; 4,830,003; 5,104,404; and 5,222,971. The modular stent-graft has three self-expanding stents; a proximal trunk stent 48, situated above the first stent-graft component at the proximal end 13A; an ipsilateral trunk stent 50, positioned within the first stent-graft component near the distal end 13B of the ipsilateral leg 15A; and a bell-bottom stent, located within the bell-bottom 42 at the distal end 13D of the contralateral leg 15B. These are self-expanding stents of the conventional type, such as disclosed in U.S. Pat. Nos. 4,580,568; 4,655,771; 4,830,003; 5,104,404; and 5,222,971. A self-expanding stent embodying limbs having at least one flat surface for providing improved expansion characteristics such as that disclosed in U.S. Pat. No. 5,993,482 can also be used.

The stents employed in the present invention are self-expanding and thus are constricted in the catheter delivery system. Since the first stent-graft component delivered to the aortic aneurysm has three stents at different levels including one above the graft, the graft (the envelope of the first stent-graft component) and stents can be quite large since they can be contracted to a very small diameter for easy delivery of the stent-graft through the ipsilateral arteries by conventional means. If two or more stents were at the same level, it would not be possible to contract the first stent-graft component to the same degree without reducing the size of the distal stents. The first stent-graft component 12 is delivered through the AAA so that the fixation device 100 is positioned suprarenally and so that the proximal end 13A of the first stent-graft component is positioned within the proximal implantation site 30 of the aorta 22. The delivery system first facilitates the affixation of the fixation device 100 at the repair site and then slowly releases the remainder of the first stent-graft component allowing the proximal trunk stent 48 to self-expand to form a union between the inner wall of the undilated portion, i.e., healthy portion, of the aorta 22 and the outer wall of the proximal end of the first stent-graft component 12. The surgeon observes this manipulation by fluoroscopic observation. As the delivery system is withdrawn, leaving the first stent-graft component in the aneurysm 28, the ipsilateral trunk stent 50 expands and then the bell-bottom stent 52 expands to form the bell-bottom. The stents 50 and 52 keep the distal ends of the legs 15A and 15B open for insertion of the second and third stent-graft components 14 and 16. The ipsilateral trunk stent 50 is optional. The ipsilateral catheter guide wire 80 utilized to guide the first stent-graft component through the ipsilateral iliac artery 24 and through the aorta aneurysm 28 to the undilated portion of the aorta 22 remains behind as a guide for the insertion, connection, and implantation of the second stent-graft component 14.

Figure 6:
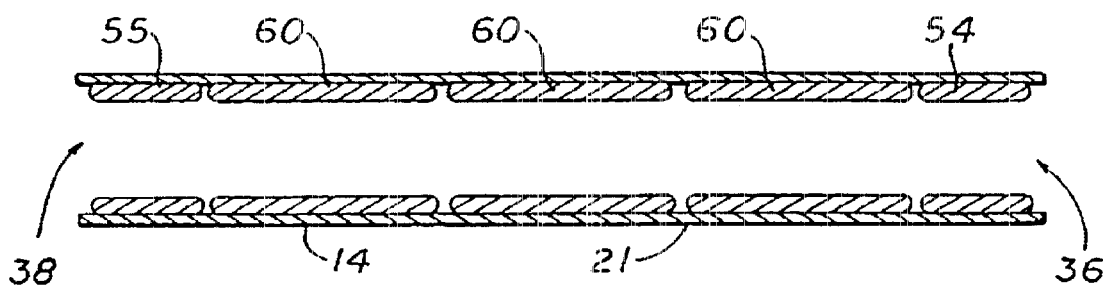
FIG. 6 is a cross-sectional view of the second stent-graft component of the modular stent-graft of FIG. 1.

The delivery system containing the contracted second stent-graft component is guided back to the AAA using the ipsilateral guide wire 80 in the same manner as the guide wire was used to implant the first stent-graft component. As shown in FIG. 6, the second stent-graft component or ipsilateral extension 14 is comprised of a tubular graft 21 with a plurality of self-expanding stents, the proximal ipsilateral extension stent 54, the distal ipsilateral extension stent 55 and supporting stents 60. Supporting stents 60 are optional. The stents are self-expanding and are contracted when inserted into the delivery system. Once the delivery system has correctly positioned the ipsilateral extension in the modular stent-graft and is withdrawn, the stents are sequentially expanded as the delivery system is withdrawn.

Referring to FIGS. 1 and 4, the proximal end 36 of the ipsilateral extension 14 is inserted into the ipsilateral docking site 18. As the delivery system is withdrawn, the proximal ipsilateral extension stent 54 expands, compressing the tubular graft 21 between the ipsilateral trunk stent 50 and the proximal ipsilateral extension stent 54. Preferentially, but not required, the internal diameter of the ipsilateral trunk stent 50 is greater than the internal diameter opening of the restriction 62, causing a narrow waist 70 to form in the graft 21 as the proximal ipsilateral extension stent 54 expands. This physically locks or secures the ipsilateral extension 14 to the ipsilateral leg 15A to prevent the ipsilateral extension from slipping out or being pulled out of the first stent-graft component. As the delivery system is fully withdrawn, the distal ipsilateral extension stent 55 expands compressing the graft 21 against the interior wall of the ipsilateral femoral artery 24 at the ipsilateral distal implantation site 32.

After the surgeon confirms that the ipsilateral extension has been successfully implanted into the ipsilateral iliac artery 24, a contralateral catheter guide wire 82 is then inserted into the AAA through the contralateral iliac artery 26. As mentioned above, the bell-bottom 42 of the first stent-graft component aids the surgeon in snaking the guide wire into the contralateral docking site 20. After the guide wire has been successfully positioned, the delivery system containing the compressed contralateral extension 16, which for all intents and purposes is identical to the ipsilateral extension shown in FIG. 6, is guided along the guide wire 82 so that the proximal end 37 of the contralateral extension is positioned within the contralateral docking site 20. The proximal end of the contralateral extension is positioned in the docking site so that the first proximal contralateral extension stent 56 is positioned above or proximal to the constriction 64 and the second proximal contralateral extension stent 58 is positioned below or distal to the constriction 64. As the delivery system is withdrawn, stents 56 and 58, which are self-expanding, expand forcing the graft 21 of the contralateral extension to expand out to compress the sheath against the inner walls of the contralateral docking site 20. Since the outer diameter of the expanded stents 56 and 58 are larger than the inner diameter of the constriction 64, a narrow waist 72 is created in the graft 21. This physically locks or secures the proximal end 37 of the contralateral extension into the docking site 20 of the first stent-graft component. After the surgeon confirms that the proximal end of the contralateral extension has been successfully connected to the contralateral docking site, the surgeon manipulates the distal end 39 of the contralateral extension into the contralateral distal implantation site 34 of the contralateral iliac artery 26. Once this positioning has been completed, the surgeon carefully withdraws the delivery system to permit the distal contralateral extension stent (not shown) to expand and compress the outer wall of the contralateral extension graft 21 against the inner wall of the contralateral femoral artery. When the surgeon confirms that the contralateral extension has been successfully implanted, the contralateral catheter guide wire is then withdrawn. At this point the modular stent-graft has been successfully implanted to repair the AAA, a repair that not only protects the life of the patient but also enhances the quality of the patient's life, since the aneurysm has been shunted out of the patient's circulatory system and no longer functions as a hydraulic accumulator.

The radioopaque marker 66 in the constriction 64 of the contralateral docking site 20 functions as a marker for the surgeon as he observes the manipulation of the various components during the operation. The marker permits the surgeon to easily locate the positioning of the proximal ipsilateral extension stent and the proximal contralateral extension stent 54, 56 respectively, with respect to the restrictions 62, 64 respectively.

Figure 7:
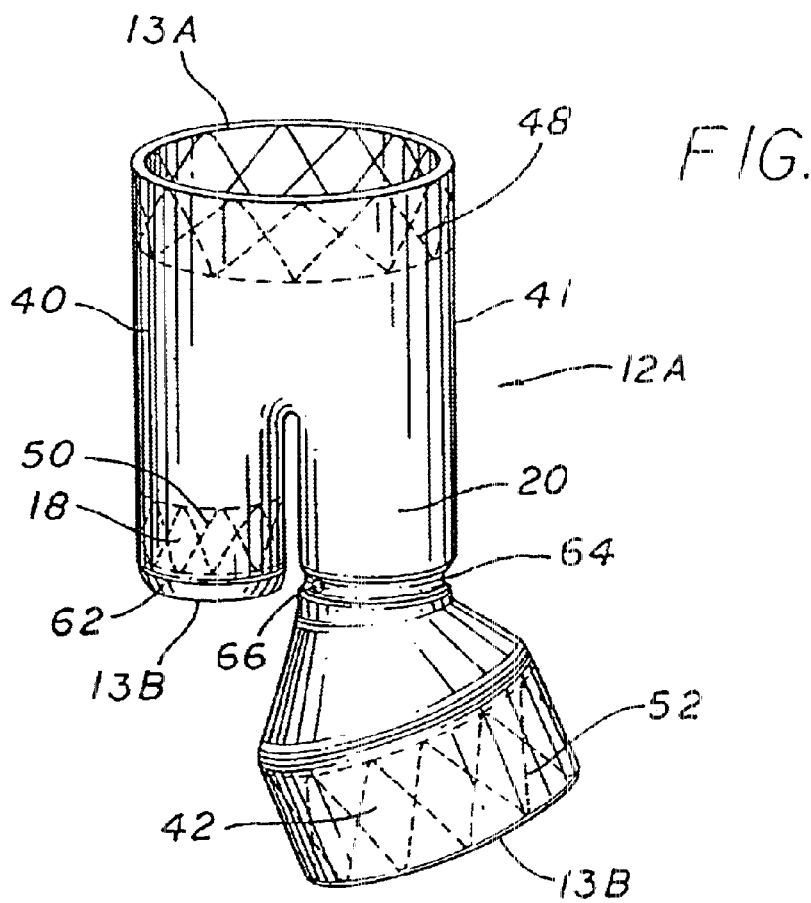
FIG. 7 is a front perspective view of an alternative embodiment of the first stent-graft component of the modular stent-graft of the present invention.

Referring to FIG. 7, an alternative embodiment of the first stent-graft component 12A of the present invention is illustrated wherein the bell-bottom 42 is angled towards the contralateral iliac orifice, making it easier to guide the contralateral catheter guide wire 82 into the contralateral docking site 20, as described above. In all other respects, the first stent-graft component is identical to the stent-graft component 12 described above. The stents 48, 50 and 52 are shown in phantom.

Figure 8:
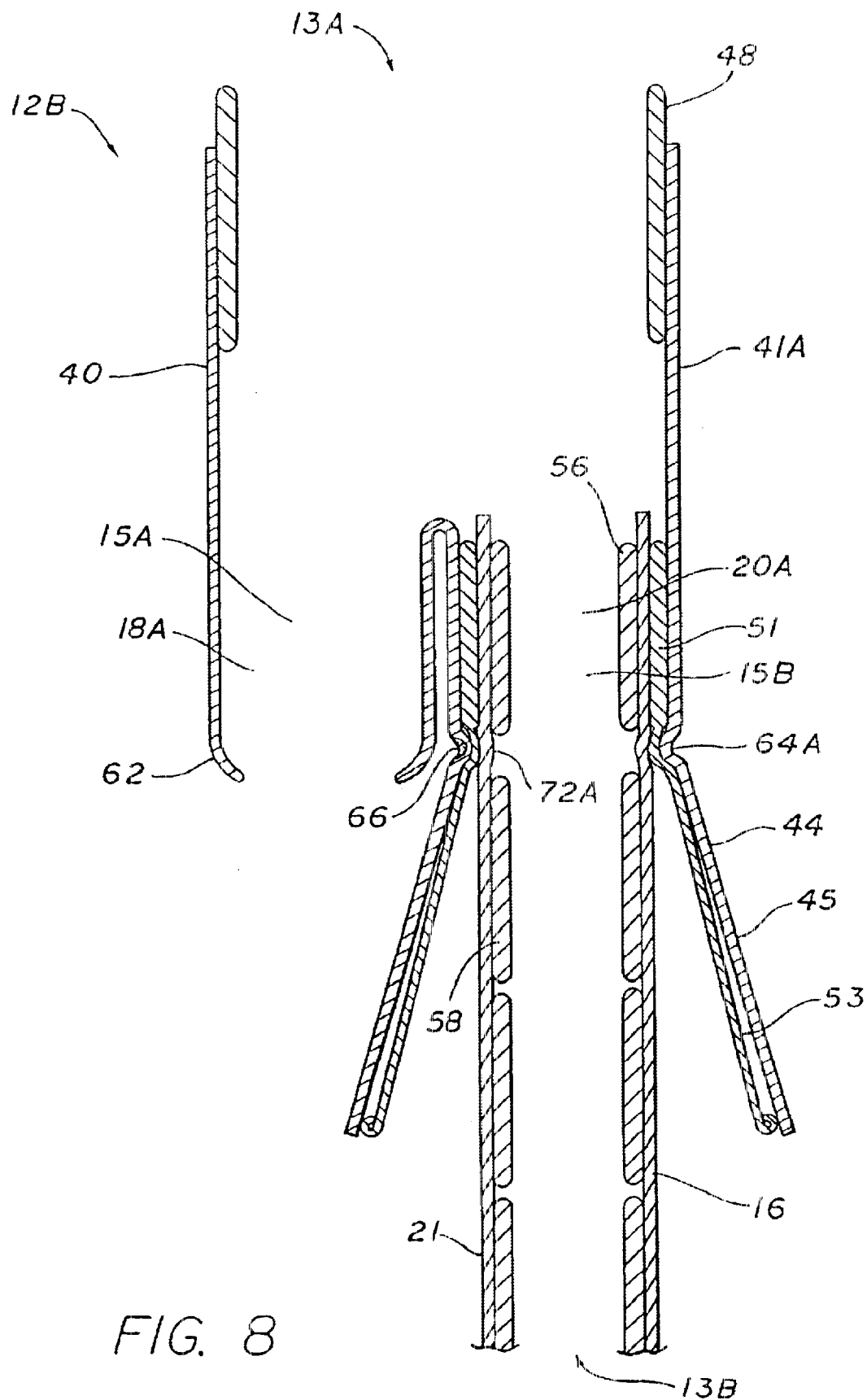
FIG. 8 is a cross-sectional view of a second alternative embodiment of the first stent-graft component of the modular stent-graft of the present invention.

Referring to FIG. 8, a second alternative embodiment of the first stent-graft component 12B of the present invention is illustrated. The ipsilateral docking site 18A is free of an ipsilateral trunk stent which is contained in the first stent-graft component 12 described above. However, the contralateral docking site 20A has a contralateral trunk stent 51 with a series of longitudinal struts 53 extending distally or downwardly from the stents 51 biased to create a conical section with respect to cone 44 of the first stent-graft component. In all other respects, the first stent-graft component 12B is identical to the first stent-graft component 12 described above.

When the alternative embodiment first stent-graft component 12B is utilized to form a modular stent-graft, the proximal end 36 of the ipsilateral extension 14 is positioned slightly above the restriction 62 so that when the proximal ipsilateral extension stent 54 expands, it expands the outer wall of the graft 21 of the ipsilateral extension against the inner wall of the ipsilateral docking site 18A to seal the ipsilateral extension to the first stent-graft component 12B.

The outer diameter of the proximal ipsilateral extension stent is greater than the inner diameter of the constriction 62 causing the graft 21 of the ipsilateral extension to form a narrow waist (not shown), thus locking and securing the proximal end of the ipsilateral extension to the ipsilateral docking site 18A to prevent the extension from slipping out or being pulled out of the first stent-graft component 12B. The cone 44 acts in the same manner as the bell-bottom 42 to give the surgeon a greater target area to locate the contralateral catheter guide wire into the contralateral docking site 20A. When the first stent-graft component 12B is in the delivery system, it is compressed and struts 53 are aligned parallel to each other and adjacent to each other. When the delivery system is withdrawn after the first stent-graft component has been implanted into the proximal implantation site 30, the struts 53 expand outwardly to expand the envelope 45 of the cone 44. The struts bow out at the juncture of the constriction 64A so as to help form the narrow waist 72A at the proximal end 37 of the contralateral extension 16. After the contralateral catheter guide wire has been positioned within the contralateral docking site 20A, the proximal end 37 of the contralateral extension 16 is positioned within the docking site. The delivery system is slowly withdrawn, allowing the proximal contralateral extension stent 56 to expand, compressing the graft 21 of the extension between the inner side of the contralateral trunk stent 51 and the outer side of the first proximal contralateral extension stent 56. The narrow waist 72A formed in the graft 21 locks or secures the proximal end 37 of the contralateral extension to the contralateral docking site 20A to prevent the extension from slipping out of being pulled out of the docking site.

Figure 9:
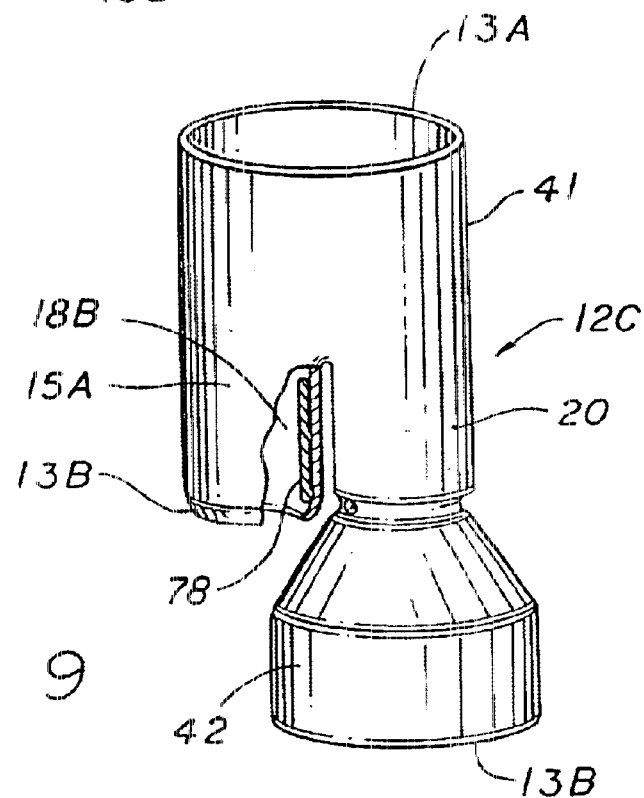
FIG. 9 is a front perspective view of a third alternative embodiment of the first stent-graft component of the modular stent-graft of the present invention.

Referring to FIG. 9, a third alternative stent-graft component 12C is illustrated which is identical to the first stent-graft component 12 described above, with the exception that ipsilateral docking site 18B of this first stent-graft component does not contain an ipsilateral front stent. In contrast, in this first stent-graft component 12C, a flexible bracer 78 is located within the component to prevent longitudinal collapse of the ipsilateral leg 15A during implantation into the proximal implantation site 30. Alternatively, longitudinal collapse of the ipsilateral leg 15A can be prevented in the first stent-graft component 12C described above by attaching ipsilateral leg 15A to contralateral leg 15B by struts attached between the two legs, a membrane attached to the two legs, or by sewing the two legs together (not shown).

A further aspect of the present invention relates to the attachment between the trunk of the graft and the aortic wall. This aspect of the invention involves axially separating an expandable framework from the graft.

Figure 10:
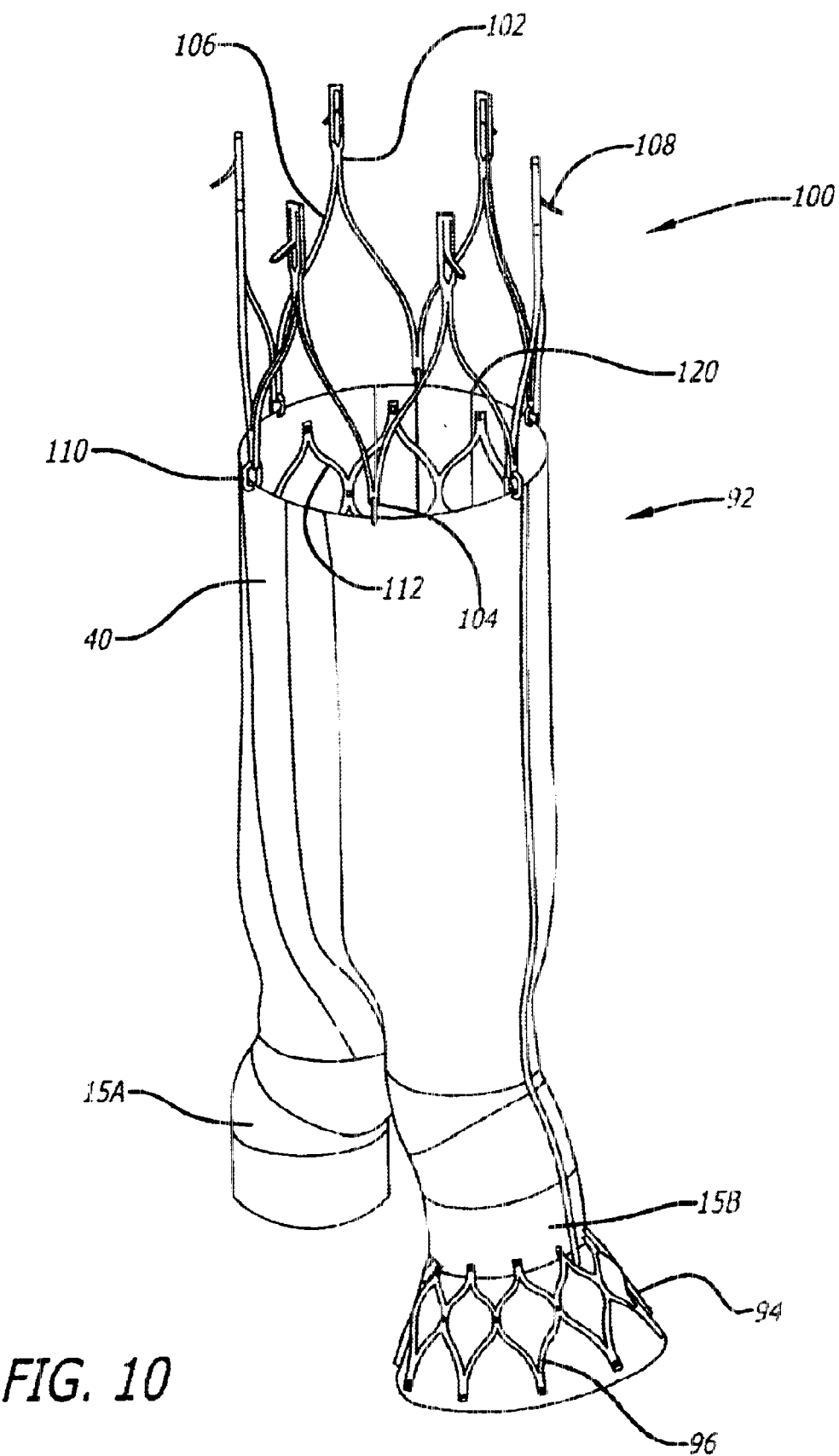
FIG. 10 is a perspective view of a further embodiment of the first stent-graft component of the present invention.

FIG. 10 exemplifies a further embodiment of the first stent-graft component 92 of the present invention, in its assembled condition before it is implanted in the patient's vasculature. As is seen in FIG. 10, the proximal trunk stent of the earlier embodiment is replaced by an expandable fixation device 100, which is positioned to be axially separated from the trunk 40 of the first stent-graft component 92, being connected to the trunk 40 by longitudinally extending members 110. As the previously described embodiment, the stent-graft component 92 may include an ipsilateral leg 15A and a contralateral leg 15B, the contralateral leg having a bell-bottom or flared configuration 94. Further, the flared end 94 is contemplated to be adapted with an external expandable stent 96 which operates to facilitate the flared configuration. It is to be recognized, however, that the stent 96 can alternatively be placed within an interior of the flared end 94.

In a preferred embodiment, the fixation device 100 is self-expanding. In alternative embodiments, the fixation device 100 may be balloon expanded. The fixation device 100 may be formed from metal which follows a generally undulating path within a cylindrical profile, thereby defining a plurality of alternating proximal apices 102 and distal apices 104 which are joined by connecting members or legs 106. Additionally, hooks 108 may be connected to the fixation device 100 to enhance its ability to attach to the aortic wall. It is contemplated that the hooks 108 are integrally formed at the proximal apices 102, but can similarly be formed at the distal apices 104 as well. The connecting legs 106 have a generally rectangular profile defined by a circumferentially extending width and a radially extending depth. In one preferred embodiment, the depth is greater than the width. When the fixation device 100 is self-expanding, its legs 106 and apices 102, 104 are urged radially outward in a direction that is at a right angle to an axis of the fixation device 100.

The fixation device 100 is contemplated to be manufactured from a continuous cylinder, into which a pattern may be cut by a laser or by chemical etching to produce slits in the wall of the cylinder. Manufacture of the preferred embodiment may additionally require stretching and annealing the fixation device 100 after it has been cut from the continuous cylinder, to give it a desired configuration. It is contemplated that the fixation device 100 be manufactured from a material having highly elastic properties such as nickel-titanium alloys since the same allows a great amount of expansion and compression of structures without permanent deformation. Implantable stainless steel is also known to be satisfactory for the purpose. An additional material from which such fixation device 100 may be manufactured is Elgiloy™ which is a chromium-cobalt-nickel alloy manufactured and sold by Elgiloy of Elgin, Ill.

The fixation device 100 is connected to the trunk 40 of the first stent-graft component 92 by a plurality of longitudinally extending members 110 which may be made from any flexible substance which is durable and biocompatible. For example, Dacron™ polyester suture material configured as ties may be suitable for forming the flexible longitudinally extending members 110. The ties 110 may be configured to loop around the distal elements forming the fixation device 100, and to penetrate the wall of the graft 112, or may be routed in any other suitable manner to form a connection between fixation device 100 and trunk 40. In one embodiment, the ties 110 may have a short length which causes the distal end of the fixation device 100 to abut the proximal end 13A of the stent-graft 92, but not to overlap it. Such an abutment may assist in preventing fluid flow around the outside of the stent-graft 92. Furthermore, as shown in FIG. 11, in yet another aspect of the invention the trunk 40 can include a plurality of proximally directed, discrete material extensions 111 with holes configured therein for receiving portions of the fixation device 100 or the longitudinally extending members 110 (not shown).

By axially separating the fixation device 100 and the trunk 40, the first stent-graft component 92 presents a more slender profile when packed in a delivery catheter than if there was an overlap, and thus may more easily be inserted into and negotiated through the patient's vasculature. This further reduces the profile obtained by separating the level of the ipsilateral trunk stent 50 (See FIG. 4) and bell bottom stent 52.

Figure 11:
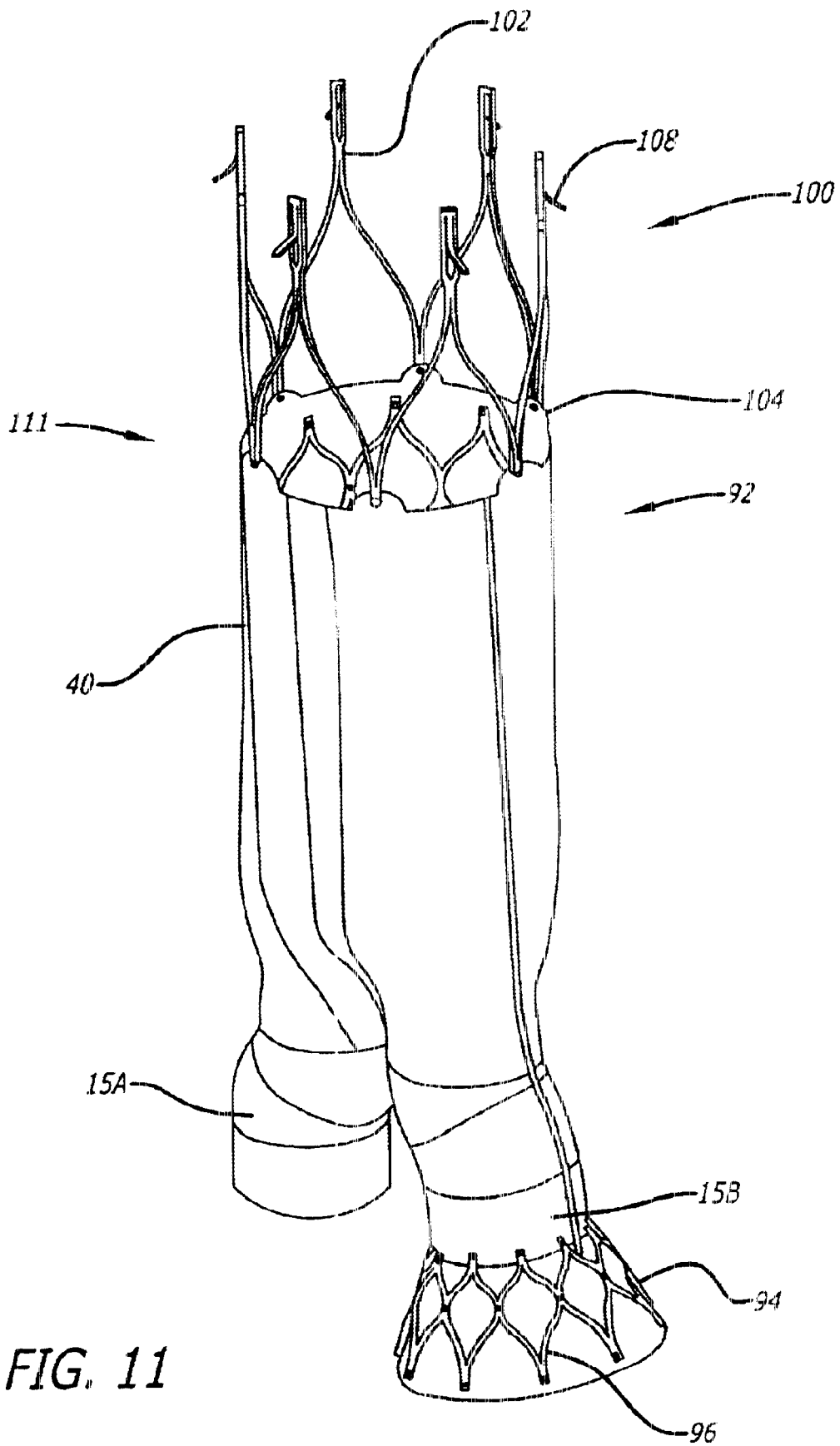
FIG. 11 is a perspective view depicting a variation of the embodiment shown in FIG. 10.

Using the methods of delivery described above, the modular stent-graft 90 of this embodiment is deployed within the vasculature, as exemplified in FIG. 11, so that the fixation device 100 is connected to healthy tissue of the aortic wall 22 above the renal arteries. Advantageously, the trunk 40 of the first stent-graft component 92 is positioned entirely distal of the fixation device 100.

In order to provide a seal between the trunk at its proximal end 120 and the vascular wall 30, one or more support structures 112 may be added to the lumen of the trunk at its proximal end portion 120 and throughout its length. Preferably, such a support structure 112 is delivered in a separate delivery catheter or loaded in a portion of the delivery catheter of the first component but at a different axial position in the delivery catheter and added after the first stent-graft component 92 has been deployed to thereby take advantage of the reduced profile achieved by separating the fixation device 100 from the trunk 40. In a preferred embodiment, the support structures 112 used in the present invention may be self-expanding, manufactured according to the same principles as the self-expanding fixation device 100. In another embodiment, the support structure 112 may be balloon-expanded.

Figure 12:
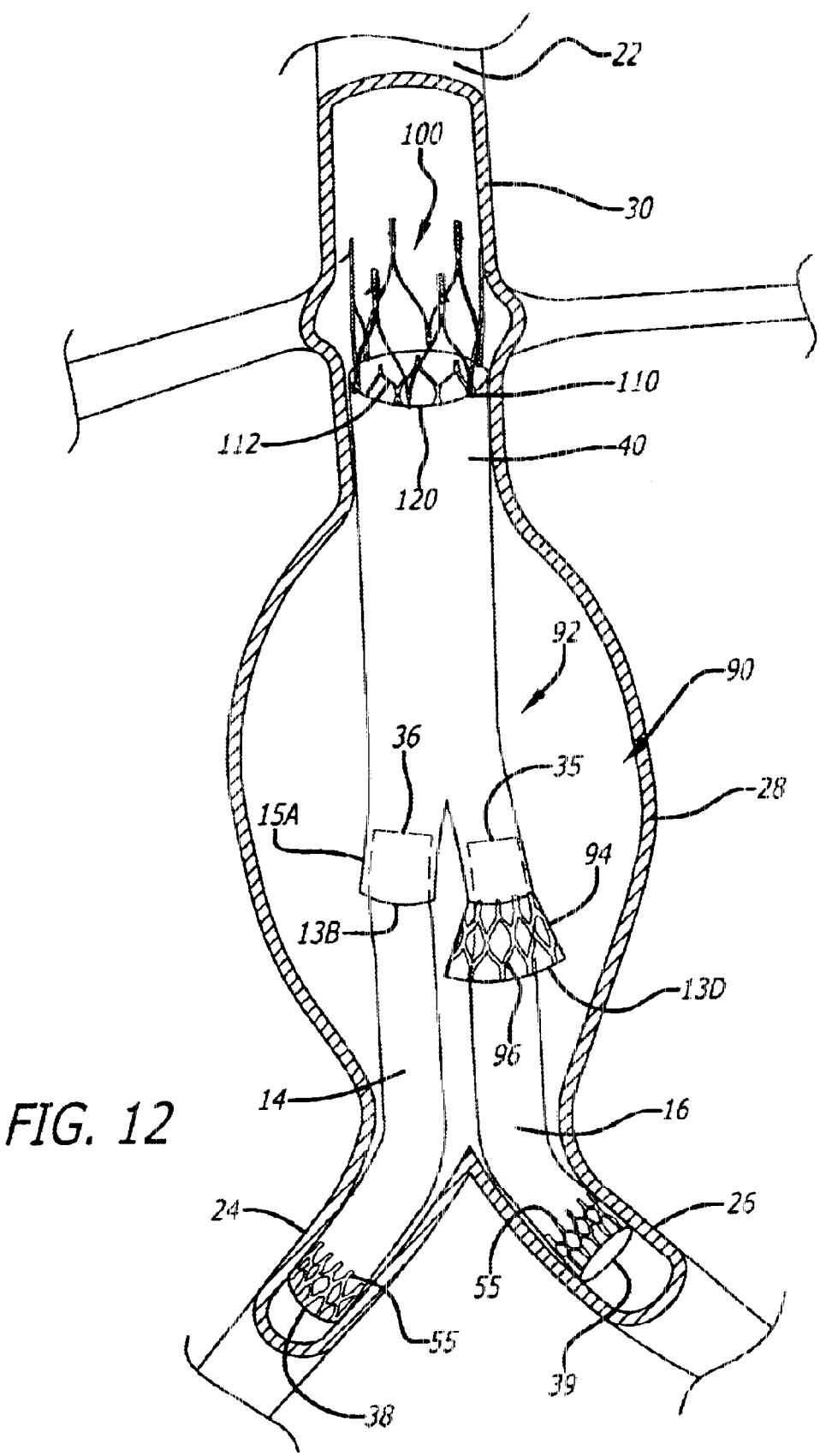
FIG. 12 is a cross-sectional view of the stent-graft of FIG. 10 implanted within vasculature in combination with extensions.

To complete the configuration of the implanted modular stent-graft 90, second and third stent-graft components 14, 16 are added to the distal ends of the legs 15A, 15B of the first stent-graft component 92, according to the methods and principles described above. FIG. 12 further exemplifies how the distal extension stents 55 may be positioned on the outside wall of the extensions 14, 16, and how the bell-bottom stent 96 may be positioned on the outside wall of the bell-bottom 94.

Figure 13:
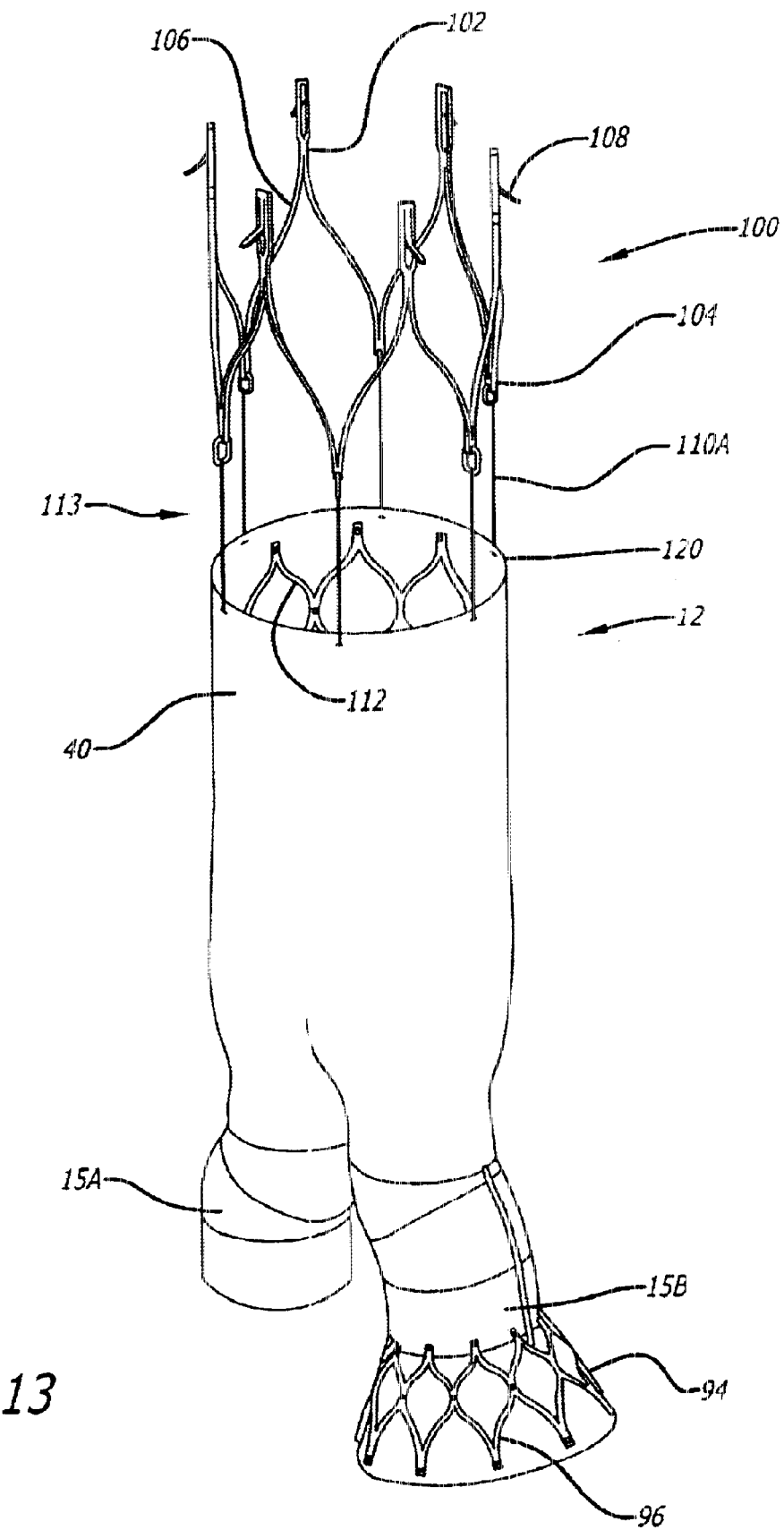
FIG. 13 is a perspective view of yet a further embodiment of the first stent-graft of the present invention.

In a further aspect of the invention, instead of short ties 110, relatively longer, substantially rigid, longitudinally extending members 110A may be used to thereby permit the fixation device and the trunk to be separated by a gap. This aspect is exemplified in FIG. 13, where the longitudinally extending members 110A provide a significant gap 113 between fixation device 100 and trunk 40. The substantially rigid longitudinally extending members 110A facilitate precise implantation by providing the device with additional stability. Alternatively, the longitudinally extending members may be of the same configuration and material as the ties described above, and therefore embody a relatively flexible material.

Figure 14:
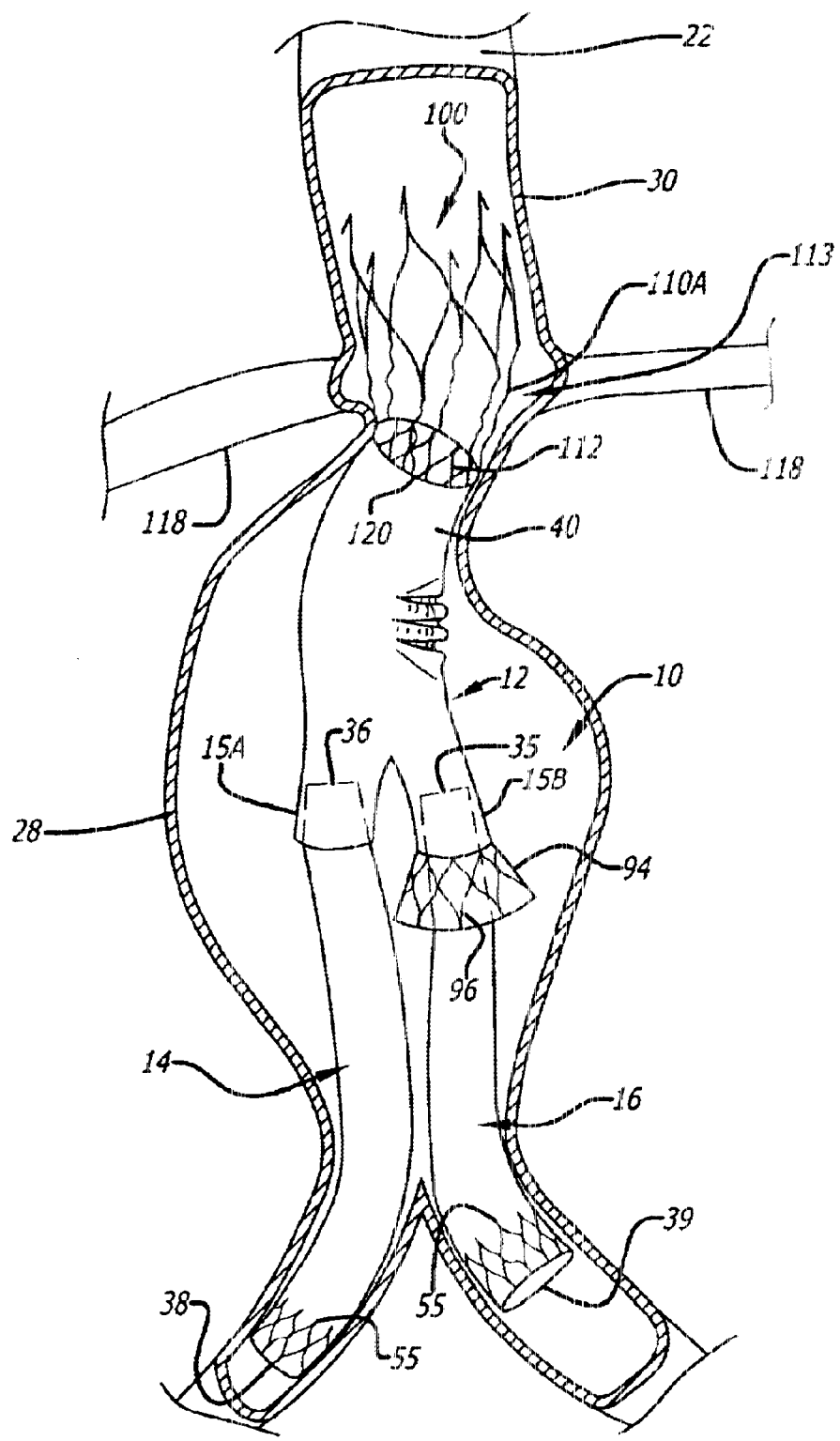
FIG. 14 is a cross-sectional view of the stent-graft of FIG. 12 with flexible longitudinally extending members and implanted within vasculature.

The advantage of increasing the extent of the separation between the graft 90 and the fixation device becomes apparent in FIG. 14, which depict how the fixation device 100 may be attached to the aortic wall 116 proximal of the renal arteries 118, allowing the trunk 40 of the first stent-graft component 92 to be positioned distal of the renal arteries 118 in a severely angulated neck. The separation of the fixation device 100 and trunk 40 is facilitated by the longitudinal extending members 110A. Positioning the fixation device 100 above the renal arteries 118 is particularly desirable when the aorta 22 below the renal arteries 118 is diseased and does not present sufficient resilience to withstand the forces which might be imposed by the fixation device 100 or otherwise required to successfully implant the stent-graft 90.

Moreover, it is frequently found that the geometry of the aorta 22 above and below the renal arteries 118 is highly irregular. For example, the diameter of the aorta 22 above the renal arteries 118 may be substantially different than the diameter below the renal arteries 118. Additionally, the aorta 22 above and below the renal arteries 118 may not share a common longitudinal axis. These irregularities may require the fixation device 100 to have a different diameter and a different axial alignment in the expanded state, than that of the stent-graft 90. The same can be accommodated by employing flexible longitudinally extending members 110A, which tend to buckle to thereby allow the stent-graft 90 to assume a position in contact with the aortic wall 116 at its proximal end-portion 120, while permitting the fixation device 100 to assume a different alignment and diameter above the renal arteries 116. Where such a misalignment is not accommodated, the wall of the trunk 40 of the first stent-graft component 92 might tend to kink at its proximal end-portion 120, thus reducing the efficacy of the seal of the graft to the vascular wall. Although axial misalignment of the proximal end 120 of the stent-graft 90 may cause kinking to take place in the wall of the graft 90 as illustrated in FIG. 14, it will be appreciated that kinking at the center of the graft 90 will likely not adversely affect the quality of the seal between graft 90 and aorta 22. It is to be recognized that although FIG. 14 shows flexible longitudinally extending members 110A, in certain circumstances, substantially rigid members may be desirable.

It has been found that, in the majority of cases, a separation 113 of up to 2 mm and as much as 10 mm or greater between the fixation device 110 and the proximal end 120 of the trunk 40 may be desirable. Such a gap 113 allows the fixation device to expand to a different diameter than the stent-graft 90 as well as to be rotated with respect to the stent-graft 90 sufficiently to accommodate expected axial misalignment which can exist in the region of the aorta 22.

As further exemplified in FIG. 14, the first stent-graft component 92 is positioned in the aorta 22 so that, when fully expanded, its proximal end 120 is located as close to the renal arteries 118 as possible, without obstructing entry to the renal arteries 118. It will be appreciated that it is imperative that renal arteries are not obstructed by the graft 90, and, accordingly, the first stent-graft component 92 should be positioned so that this condition is met. It will be further appreciated that the elements forming the fixation device 100 and the longitudinally extending members 100, 110A may be allowed to overlay the entry to the renal arteries 118 without ill effect, where they are not sufficiently large to cause any appreciable reduction in blood flow to the renal arteries 118.

Figure 15:
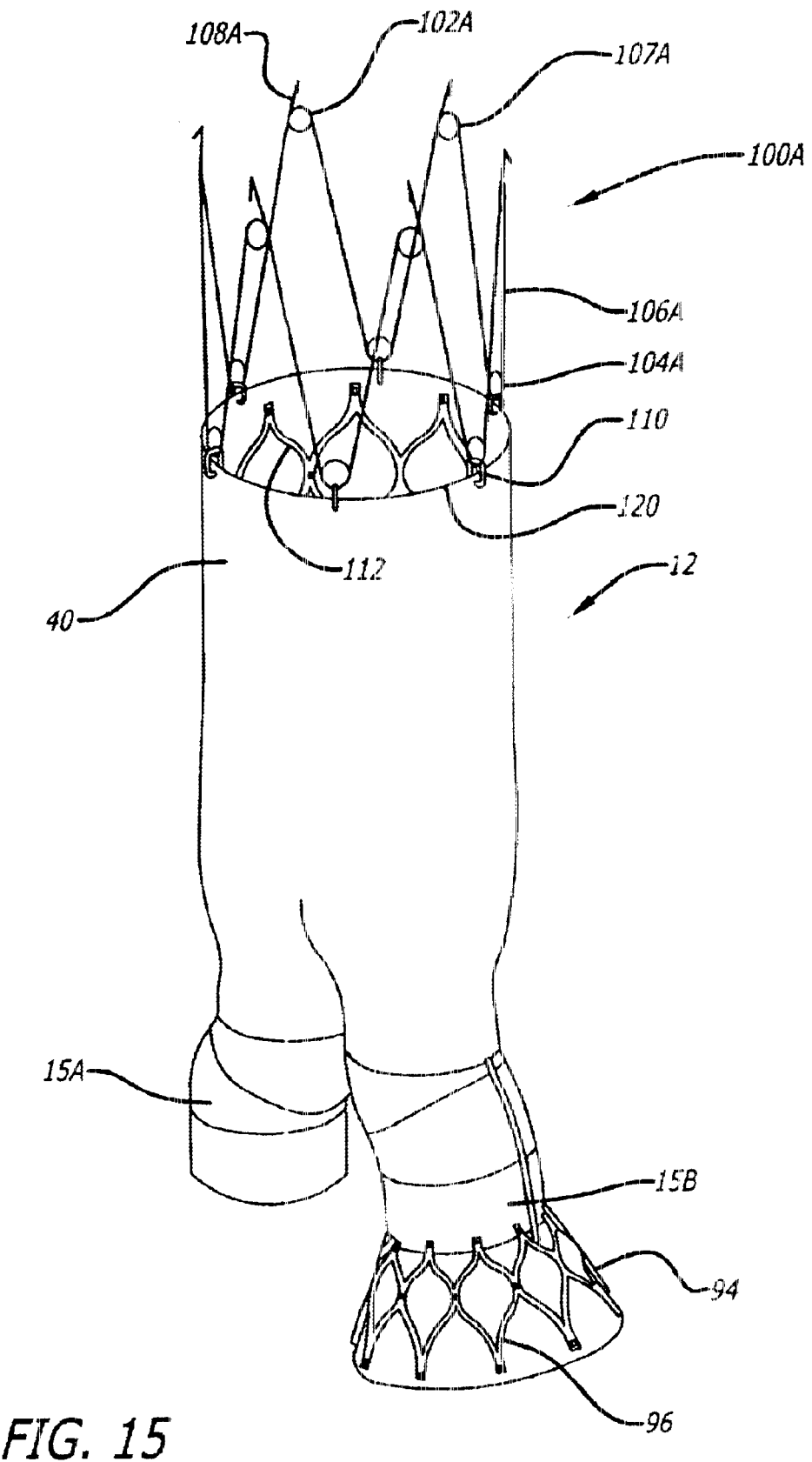
FIG. 15 is a perspective view of another further embodiment of the stent-graft of the present invention.

With reference to FIG. 15, an alternate embodiment of a fixation device 100A is shown. The fixation device 100A may be manufactured from a single piece of wire, which is formed by looping the wire around pins appropriately spaced and attached to a cylindrical mandrel. The two ends of the wire may be welded or glued together to form a continuous framework within a cylindrical profile. The configuration of the present variation similarly has proximal apices 102A and distal apices 104A connected by legs or members 106A. Each of the apices 102A, 104A may further embody a helix 107A. Further, hooks 108A may be added to the fixation device 100A to enhance attachment to the vascular wall. Suitable material from which the fixation device of this embodiment may be made include Nitinol and Elgiloy™.

Figure 16:
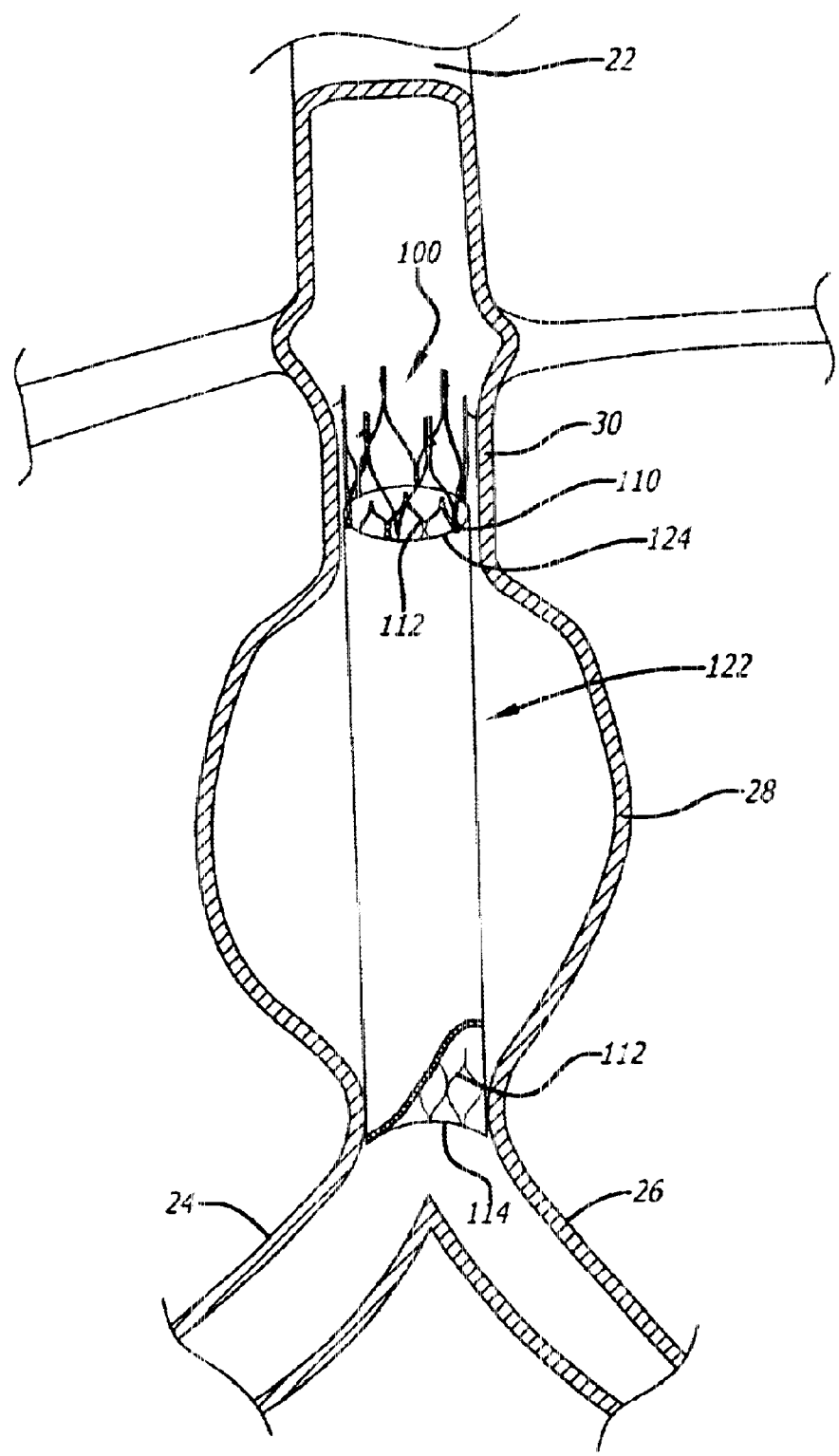
FIG. 16 is a cross-sectional view of a variation of the stent-graft of the present invention.

In another aspect of the invention, the principle of separating the fixation device from the graft may be applied to grafts which are not bifurcated modular grafts, but which are bifurcated or cylindrical unitary grafts. FIG. 16 exemplifies this variation, and shows a fixation device 100 of earlier described embodiment connected to a cylindrical graft 122 according to the same principles described above, in which ties 110 may be used to achieve the connection. This aspect of the invention contemplates that flexible longitudinally extending members such as those (110A) already described above, may also be used where required. This embodiment of the invention may bused where the quality of aortic tissue at the proximal end 124 of the cylindrical graft 122 permits a seal to be formed with the aorta 22. Such a seal may be formed using the same type of support structure 112 as earlier described to seal the proximal end 124 of the graft 122 to the aorta 22. The fixation device can be implanted as shown or can be implanted above the renals such that the top edge of the graft is just below the renal artery openings.

It will be apparent from the foregoing that, while particular forms of the invention have been illustrated and described, various modifications can be made without departing from the spirit and scope of the invention.

Accordingly, it is not intended that the invention be limited, except as by the appended claims.

We claim:

1. A device for repairing a corporeal vessel having a wall defining an internal lumen, comprising:
   a graft having a wall defining a lumen and including a plurality of discrete material extensions, said graft being adapted to be expandable from a collapsed condition to an expanded condition; and
   a fixation device connected to said graft by a plurality of ties, said fixation device being adapted to be expandable from a compressed condition to an expanded condition, said fixation device being positioned longitudinally separated from said graft when said fixation device is in said expanded condition.

2. The device of claim 1, wherein said fixation device abuts said graft.

3. The device of claim 1, wherein said fixation device is self-expanding.

4. The device of claim 1, wherein said fixation device is balloon-expanded.

5. The device of claim 1, wherein said fixation device is formed from a metal cylinder.

6. The device of claim 1, wherein said fixation device is formed from a metal wire.

7. The device of claim 1, said graft further comprising at least one terminal end configured with a bell bottom profile.

8. The device of claim 1, wherein the ties are flexible longitudinally extending members configured to attach said fixation device to said graft.

9. The device of claim 8, wherein there are at least three flexible longitudinally extending members.

10. The device of claim 1, the plurality of discrete material extensions each having an apex, at least one longitudinally extending member being substantially aligned with at least one apex of the plurality of discrete material extensions.

11. The device of claim 1, wherein said fixation device is formed of a nickel-titanium alloy.

12. The device of claim 1, wherein said fixation device is formed of a chromium-cobalt-nickel alloy.

13. The device of claim 1, additionally comprising at least one support structure being separate from said graft and said fixation device and adapted to be expandable from a collapsed condition to an expanded condition within said lumen of said graft.

14. The device of claim 13, wherein said support structure is self-expanding.

15. The device of claim 13, wherein said support structure is balloon expanded.

16. The device of claim 1, wherein said graft has a modular configuration.

17. The device of claim 16, said graft further comprising at least one graft extension, said graft extension attached to said graft in vivo.

18. The device of claim 1, wherein said graft has a bifurcated configuration.

19. The device of claim 1, said fixation device further comprising a plurality of proximal and distal apices joined by connector members.

20. The device of claim 19, wherein said connecting member has a rectangular cross-sectional profile.

21. The device of claim 1, said graft further comprising:
   a bifurcated first tubular component having a trunk portion with first and second legs extending therefrom;
   a second tubular component configured to mate with said first leg; and
   a third tubular component configured to mate with said second leg.

22. The device of claim 21, wherein said second leg extends beyond said first leg.

23. The device of claim 22, wherein said second leg includes an end-portion which has a bell-bottom configuration.

24. The device of claim 22, said first tubular component further comprising:
   a first stent configured to be attached to said first leg; and
   a second stent configured to be attached to said second leg;
   wherein said first stent is longitudinally displaced from said fixation device, and said second stent is longitudinally displaced both from said fixation device and from said first stent.

* * * * *

UNITED STATES PATENT AND TRADEMARK OFFICE
CERTIFICATE OF CORRECTION

PATENT NO.    : 6,652,580 B1                                                Page 1 of 1
DATED         : November 25, 2003
INVENTOR(S)   : Timothy A. M. Chuter, David T. Pollock and Tamara L. Trayer It is certified that error appears in the above-identified patent and that said Letters Patent is hereby corrected as shown below:

Column 1,
Line 31, delete "lilac" and insert -- iliac --.

Column 3,
Line 20, delete "and" before "can".
Line 32, insert -- the -- before "vascular".

Column 4,
Line 44, delete "stet-graft" and insert -- stent-graft --.

Column 8,
Line 47, delete "of" and insert -- or --.

Column 10,
Line 46, delete "96" and insert -- 92 --.

Column 12,
Line 16, insert -- , -- after "members".
Line 18, delete "bused" and insert -- be used --.
Line 63, delete "1" and insert -- 8 --.
Line 64, insert -- of the -- after "one".

Column 13,
Lines 24-25, delete "connecting member has" and insert -- connector members have --.

Signed and Sealed this

First Day of June, 2004

JON W. DUDAS
*Acting Director of the United States Patent and Trademark Office*